(12) United States Patent
Bortz et al.

(10) Patent No.: US 9,339,475 B2
(45) Date of Patent: *May 17, 2016

(54) SPATIAL ARRANGEMENT OF PARTICLES IN A DRINKING DEVICE FOR ORAL DELIVERY OF PHARMACEUTICALS

(71) Applicant: Particle Dynamics International, LLC, St. Louis, MO (US)

(72) Inventors: Jonathan David Bortz, St. Louis, MO (US); Yury Lagoviyer, Olivette, MO (US); Paul Timothy Brady, St. Louis, MO (US)

(73) Assignee: Particle Dynamics International, LLC, St. Louis, MO (US)

( * ) Notice: Subject to any disclaimer, the term of this patent is extended or adjusted under 35 U.S.C. 154(b) by 13 days.

This patent is subject to a terminal disclaimer.

(21) Appl. No.: 14/170,927

(22) Filed: Feb. 3, 2014

(65) Prior Publication Data

US 2014/0212505 A1 Jul. 31, 2014

Related U.S. Application Data

(63) Continuation of application No. 12/032,964, filed on Feb. 18, 2008, now Pat. No. 8,679,541.

(60) Provisional application No. 60/894,759, filed on Mar. 14, 2007.

(51) Int. Cl.
*A61K 9/00* (2006.01)
*A61K 9/50* (2006.01)

(52) U.S. Cl.
CPC ................ *A61K 9/50* (2013.01); *A61K 9/0095* (2013.01)

(58) Field of Classification Search
None
See application file for complete search history.

(56) References Cited

U.S. PATENT DOCUMENTS

| | | |
|---|---|---|
| 4,180,560 A | 12/1979 | Katz et al. |
| 4,438,091 A | 3/1984 | Gruber et al. |
| 4,790,820 A | 12/1988 | Theeuwes |
| 4,865,585 A | 9/1989 | Theeuwes |
| 4,921,713 A | 5/1990 | Fowler |
| 4,981,468 A | 1/1991 | Benefiel et al. |
| 4,985,017 A | 1/1991 | Theeuwes |
| 5,014,750 A | 5/1991 | Winchell et al. |
| 5,068,112 A | 11/1991 | Samejima et al. |
| 5,069,671 A | 12/1991 | Theeuwes |
| 5,094,861 A | 3/1992 | D'Auguste et al. |
| 5,320,853 A | 6/1994 | Noda et al. |
| 5,378,232 A | 1/1995 | Easton et al. |
| 5,405,631 A | 4/1995 | Rosenthal |
| 5,445,829 A | 8/1995 | Paradissis et al. |
| 5,466,465 A | 11/1995 | Royds et al. |
| 5,494,681 A | 2/1996 | Cuca et al. |
| 5,866,185 A | 2/1999 | Burkett |
| 5,910,321 A | 6/1999 | Wong et al. |
| 5,919,368 A | 7/1999 | Quinn et al. |
| 5,985,324 A | 11/1999 | Wong et al. |
| 5,989,590 A | 11/1999 | Wong et al. |
| 6,096,003 A | 8/2000 | Wong et al. |
| 6,103,265 A | 8/2000 | Wong et al. |
| 6,106,845 A | 8/2000 | Wong et al. |
| 6,109,538 A | 8/2000 | Villani et al. |
| 6,210,713 B1 | 4/2001 | Wong et al. |
| 6,284,270 B1 | 9/2001 | Lagoviyer et al. |
| 6,465,010 B1 | 10/2002 | Lagoviyer et al. |
| 6,482,451 B1 | 11/2002 | Baron |
| 6,541,055 B1 | 4/2003 | Luzenberg |
| 6,572,582 B1 | 6/2003 | Wong et al. |
| 6,605,303 B1 | 8/2003 | Karehill et al. |
| 6,866,863 B2 | 3/2005 | Ribi |
| 7,077,175 B2 | 7/2006 | Yin et al. |
| 7,399,485 B1 | 7/2008 | Shimizu et al. |
| D578,333 S | 10/2008 | Baron |
| D602,726 S | 10/2009 | Baron |
| 7,790,755 B2 | 9/2010 | Akiyama et al. |
| 2002/0038066 A1 | 3/2002 | Strangio et al. |
| 2003/0021842 A1 | 1/2003 | Lagoviyer et al. |
| 2003/0039685 A1 | 2/2003 | Yanagisawa et al. |
| 2003/0203027 A1 | 10/2003 | Verreck et al. |
| 2004/0247677 A1 | 12/2004 | Oury et al. |
| 2004/0265372 A1 | 12/2004 | Wynn et al. |
| 2007/0193894 A1* | 8/2007 | Macken et al. ............... 206/219 |
| 2009/0041904 A1 | 2/2009 | Baron |

FOREIGN PATENT DOCUMENTS

| | | |
|---|---|---|
| WO | 0006126 | 2/2000 |
| WO | 2004035020 | 4/2004 |
| WO | WO2005084685 | * 9/2005 |

OTHER PUBLICATIONS

Ambros et al, The Characterization of the Mechanical Stength of Chewable Tablets, Pharmaceutical Development and Technology, 3(4), 509-515 (1998).

Melgoza, L.M., et al., "Estimation of the Percolation Thresholds in Dextromethorphan Hydrobromide Matrices," 2001, Eur J Pharma Sci, 12:453-459.

PCT Notification of the International Search Report and the Written Opinion of the International Searching Authority or the Declaration for PCT/US2008/054218.

* cited by examiner

*Primary Examiner* — Jennifer A Berrios
(74) *Attorney, Agent, or Firm* — Senniger Powers LLP

(57) ABSTRACT

The present invention relates to spatially arranging a plurality of particles in a device for the oral delivery of a pharmaceutical. In particular, the plurality of particles is utilized for the oral delivery of a pharmaceutical to a subject via the drinking device.

20 Claims, 7 Drawing Sheets

A

B

C

SPATIAL ARRANGEMENT OF PARTICLES IN A DRINKING DEVICE FOR ORAL DELIVERY OF PHARMACEUTICALS

This application is a continuation application of U.S. Ser. No. 12/032,964, filed Feb. 18, 2008, issued as U.S. Pat. No. 8,679,541 on Mar. 25, 2014, which claims the benefit of U.S. provisional patent application Ser. No. 60/894,759, filed on Mar. 14, 2007, the entire disclosures of which are incorporated herein by reference for all relevant purposes.

FIELD OF THE INVENTION

The present invention relates to spatially arranging a plurality of particles in a device for the oral delivery of a pharmaceutical.

BACKGROUND OF THE INVENTION

For optimal pharmacotherapy, it is important to achieve maximum patient compliance. Compliance is dependent on a number of factors including but not limited to the route and frequency of drug administration. Frequency of administration can sometimes be decreased by administering long-acting, sustained release, or controlled release pharmaceutical formulations. These techniques have been of tremendous benefit, especially for oral administration. But oral dosage forms themselves oftentimes have serious disadvantages that adversely affect patient compliance.

Oral dosage forms present significant drawbacks for several classes of patients. Many patients are unable or unwilling to swallow a solid dosage form. This problem occurs primarily in children and the elderly, however, problems with swallowing are not limited to those segments of the population. Certain conditions or disease states manifest themselves by swallowing difficulties. Otherwise healthy individuals can also exhibit problems with swallowing. Such swallowing difficulties, irrespective of their cause, can severely compromise patient compliance. Swallowing difficulties are also problematic when medicating animals. The taste of an oral formulation, whether solid or liquid, may also affect compliance. Many individuals, and children in particular, refuse to ingest an oral dosage form that has a bitter, sour, metallic, or generally unpleasant taste.

While the pharmaceutical industry has long-recognized the need for a satisfactory alternative to oral dosage forms, none have materialized. Syrups, elixirs, microcapsules containing slurries, chewable tablets and other novel tablet or capsule dosage forms have been developed. None of these dosage forms have been ideal and each has their own disadvantages. To improve patient compliance, therefore, a need remains for an oral delivery composition that is easy to swallow.

SUMMARY OF THE INVENTION

Accordingly, one aspect of the invention provides a plurality of particles wherein each particle comprises a pharmaceutically active agent. The particles are generally spatially arranged in a device to achieve a specific flow resistance not greater than about 50 Torr/mm such that a dosage comprising an effective amount of the pharmaceutically active agent is orally delivered to a subject as fluid flows over the plurality of particles.

Another aspect of the invention encompasses a plurality of particles wherein each particle comprises a pharmaceutically active agent. The particles are typically spatially arranged in a device so that the interstitial porosity of the bed is not less than about 5% such that a dosage comprising an effective amount of the pharmaceutically active agent is orally delivered to a subject as fluid flows over the plurality of particles.

Yet another aspect of the invention provides a plurality of particles wherein each particle comprises a pharmaceutically active agent. Typically, the particles have a tensile strength of not less than about 0.01 MPa, and a friability of not more than about 15%. The particles are generally spatially arranged in a device such that a dosage comprising an effective amount of the pharmaceutically active agent is orally delivered to a subject as fluid flows over the plurality of particles.

Other aspects and iterations of the invention are described in more detail hereinafter.

FIGURES

Figure 3:
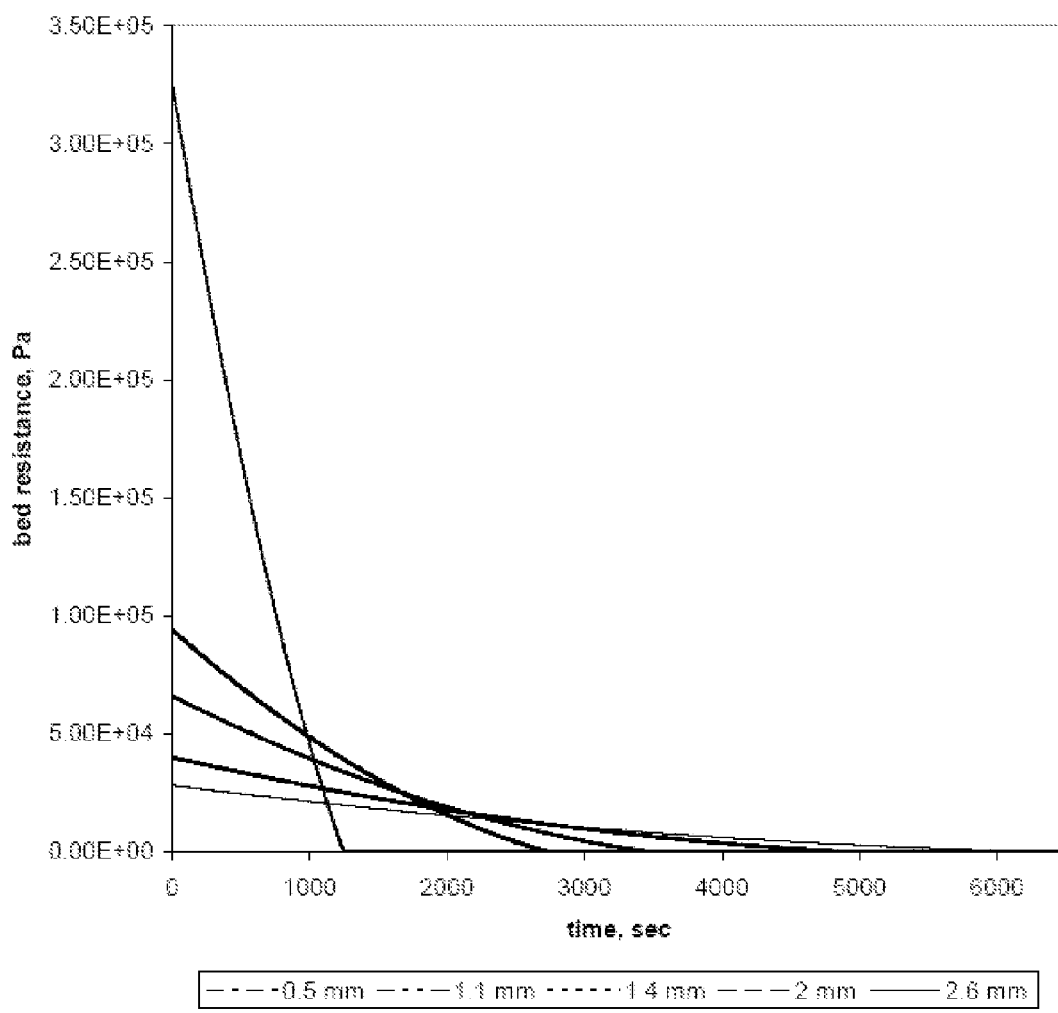

FIG. 3 is a graph depicting the decrease in flow resistance over "sip" time. The drinking devise has a plurality of particles with "close" packing, and the "sip" rate was 250 ml/min. The drop in pressure is plotted for particles of different diameters. The intercept of any given kinetic curve with the abscissa of the graph indicates the complete dissolution of the particles.

Figure 4:
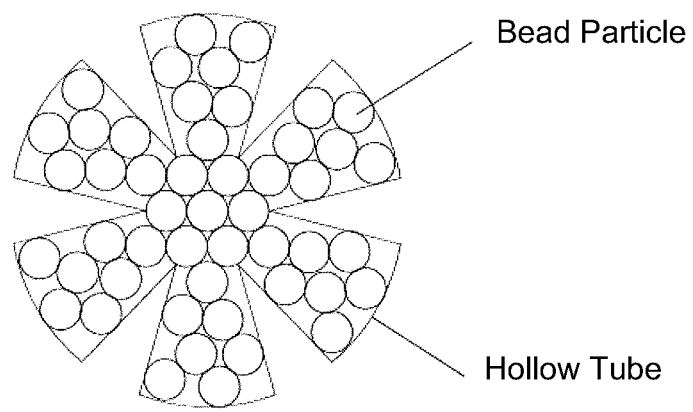
Figure 4:
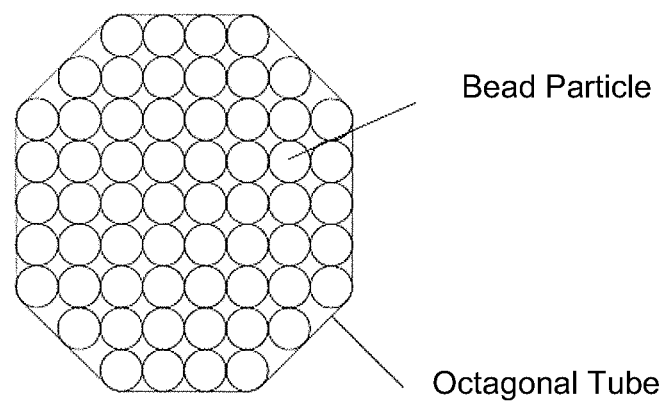
Figure 4:
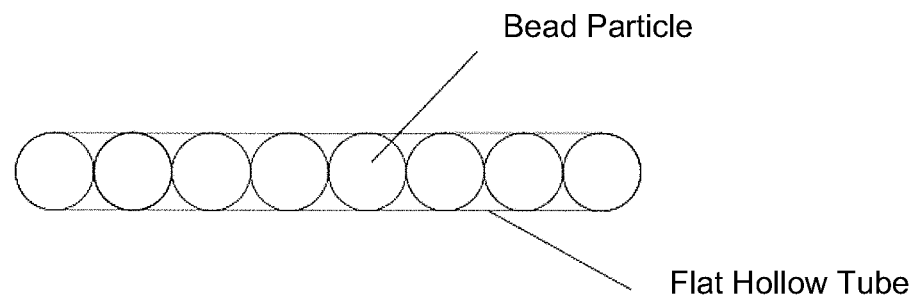

FIG. 4 presents alternate designs for the drinking device. All views are in cross section. (A). Hollow tube with ribs or baffles. (B). Octagonal hollow tube. (C) Flat hollow tube.

Figure 5:
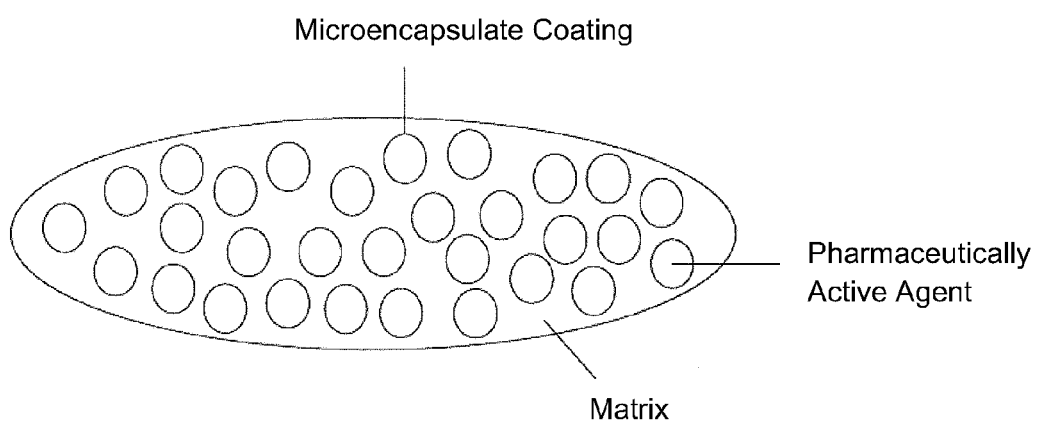

FIG. 5 is a schematic depicting an embodiment of an oral delivery composition with no inner core.

Figure 6:
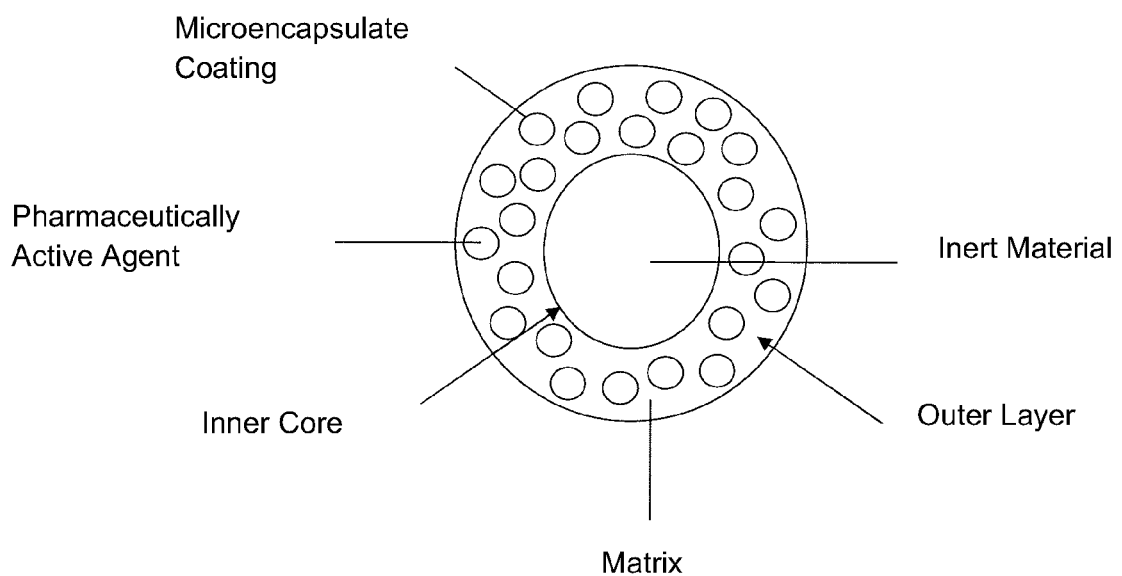

FIG. 6 is a schematic depicting an embodiment of an oral delivery composition having an inner core.

Figure 7:
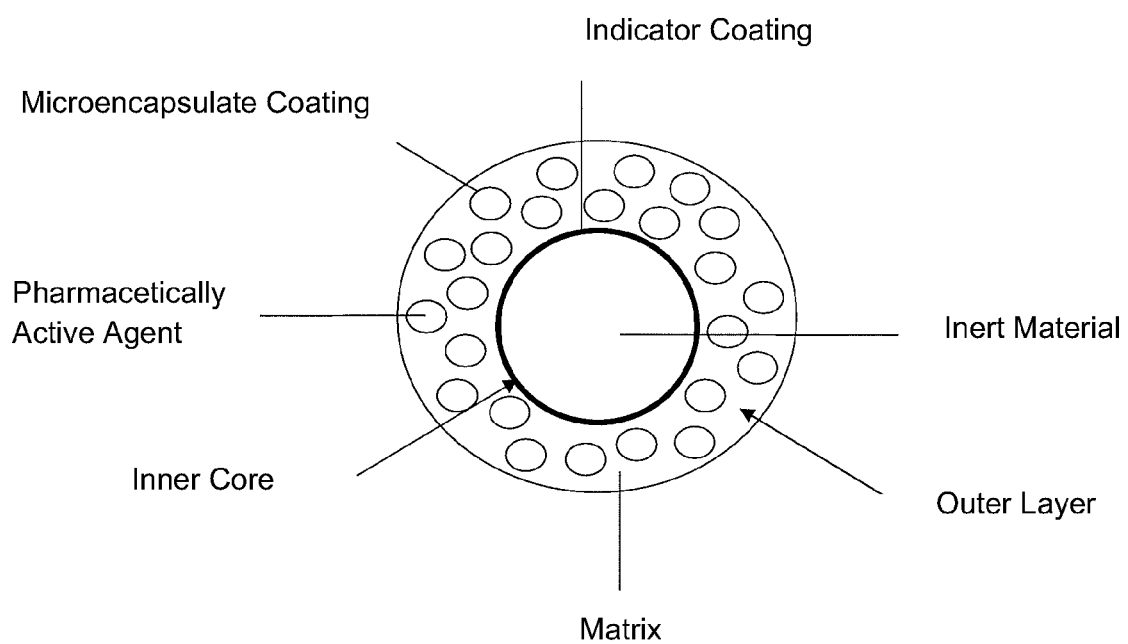

FIG. 7 is a schematic depicting an embodiment of an oral delivery composition having an inner core with an indicator coating.

DETAILED DESCRIPTION OF THE INVENTION

The present invention provides methods for spatially arranging a plurality of particles in a drinking device. In particular, the plurality of particles is utilized for the oral delivery of a pharmaceutical to a subject via the drinking device. The particles comprise pharmaceutically active agents that are typically released when the particles are contacted with an aqueous medium. As such, when fluid flows through the drinking device containing the particles, the pharmaceutically active agent is released into the fluid, which may be imbibed by a subject through the drinking device. Because the pharmaceutically active agents utilized in the invention are generally less than about 200 microns, the drinking device may be advantageously used to orally administer drugs, vitamins, or minerals to subjects that have difficulty swallowing capsules or tablets, such as pediatric or elderly subjects.

(I) Particles

One aspect of the invention encompasses a plurality of particles that may be spatially arranged within a drinking device such that an accurate dosage of a pharmaceutical may be administered to a subject. The particles typically comprise at least one pharmaceutical agent, may optionally include an excipient or mixtures of excipients, and may optionally include an indicator coating. Alternatively, the particles may be a mixture of particles having a pharmaceutical agent and particles not having a pharmaceutical agent. The pharmaceutical agent, excipient(s), and indicator coating may be embedded in the particle, may be contained within the particle, and may be combinations thereof. Each feature of the particles is described in more detail below.

(a) Physical Properties of the Particles

The particle may be constructed from a variety of suitable excipients or combinations of excipients. Suitable excipients typically will yield a particle that releases the pharmaceutical agent when contacted with an aqueous medium. The particle may substantially be comprised of a carbohydrate. The carbohydrate may be a polyol, low molecular weight saccharide, or any combination of materials, such as OraQuick Matrix, described in U.S. Pat. Nos. 6,284,270 and 6,465,010, both of which are hereby incorporated by reference in their entirety. Non-limiting examples of suitable carbohydrates include, mannitol, mannose, sorbitol, xylitol, xylose, dextrose, sucrose, lactose, glucose, fructose, and combinations thereof.

In the context of the invention, "release" of the pharmaceutical agent means that the particle may dissolve, disintegrate, or disperse when contacted with an aqueous medium and concomitantly, will then generally release the pharmaceutically active agent into the aqueous medium. Without being bound to any particular limitation, the particle will typically substantially release the pharmaceutically active agent within from about one second to about five minutes (i.e., 300 seconds) after being contacted with an aqueous medium. The particle may release the pharmaceutically active agent in from about 1 to about 30 seconds, from about 30 to about 60 seconds, from about 60 to about 90 seconds, from about 90 to about 120 seconds, from about 120 to about 150 seconds, from about 150 to about 180 seconds, from about 180 to about 210 seconds, from about 210 to about 240 seconds, from about 240 to about 270 seconds, from about 270 to about 300 seconds, or greater than about 300 seconds after the particle has been contacted with an aqueous medium.

Generally speaking, the particle will have a tensile strength and friability such that the particles can readily maintain their structural integrity as fluid flows over them in the drinking device at a specific flow resistance ranging from about 0 to about 50 Torr/mm, but yet the particles will be soft enough to ensure delivery of an accurate dosage of the pharmaceutical agent. The tensile strength is typically not less than about 0.01 MPa. In certain embodiments, the tensile strength may range from about 0.1 to about 50 MPa. In still another embodiment, the tensile strength may range from about 0.1 to about 10 MPa. In yet another embodiment, the tensile strength may range from about 0.5 to about 5 MPa. The friability is typically not more than about 15%. In certain embodiments, the friability may range from about 0% to about 15%. In another embodiment, the friability may range from about 0% to about 5%. In still another embodiment, the friability may range from about 0.01% to about 0.2%.

As will be appreciated by a skilled artisan, depending upon the embodiment, the particle may be in the form of either a continuous phase or in a discontinuous phase. Examples of particles in a continuous phase include glassy, amorphous, and monocrystalline solids and semisolids. Alternatively, examples of particles in a discontinuous phase include singe phase particles bound to each other by e.g., either crystalline bridges and/or by other physical forces (e.g., Van der Waals or electrostatic). In this context, the chemical nature of the particle may be individual compounds, inclusion complexes, adsorbed onto a carrier phase, and ion exchange bound without departing from the scope of the invention.

The size and shape of the particles can and will vary. They may be regularly shaped, irregularly shaped, round, spherical, and combinations thereof. The average diameter of the composition may be on a nanoscale, microscale, or macroscale. For example, the size may vary from about 1 mm to about 2 cm. The size may be from less than about 1 mm, from about 1 to about 2 mm, from about 2 to about 4 mm, from about 4 to about 6 mm, from about 6 to about 8 mm, from about 8 to about 10 mm, from about 10 to about 12 mm, from about 12 to about 14 mm, from about 14 to about 16 mm, from about 16 to about 18 mm, from about 18 to about 20 mm, or greater than about 20 mm.

(b) Exemplary Particles

Referring to FIGS. 5, 6, and 7, in an exemplary embodiment, the particles comprise an outer layer formed over an inner core. The outer layer has a plurality of pharmaceutically active agents embedded in a matrix that is substantially erodable when contacted with an aqueous medium. Alternatively, the pharmaceutically active agents may be encapsulated by a coating. The inner core generally comprises an inert material. As shown in FIG. 7, an indicator coating may be formed over the inner core and disposed between the inner core and the outer layer. Alternatively, as depicted in FIG. 5, the particle may comprise an outer layer with no inner core. In this context, the particle generally comprises a plurality of pharmaceutically active agents embedded in a matrix that is substantially erodable when contacted with an aqueous medium. In certain alternatives of this embodiment, the pharmaceutically active agents may be encapsulated. The physical parameters of the particles for this embodiment, such as size, shape, chemical nature, hardness, friability, and release rate of the pharmaceutical, are the same as detailed in (I)(a).

i Outer Layer

The outer layer generally comprises a matrix and a plurality of pharmaceutically active agents that are typically embedded in the matrix. Optionally, the outer layer may also include additional excipients. Suitable excipients are detailed in (I)(c) and suitable pharmaceutically active agents are detailed in (I)(d).

The matrix may be constructed from a variety of suitable excipients or combinations of excipients. By way of non-limiting example, any of the carbohydrates detailed in (I)(a) above may be used to form the matrix. As detailed above, suitable excipients typically will yield a matrix that is substantially erodable when contacted with an aqueous medium. In this context, "substantially erodable" means that the matrix typically will dissolve, disintegrate, or disperse when contacted with an aqueous medium and concomitantly, will then generally release the embedded pharmaceutically active agent or encapsulated pharmaceutically active agent. The pharmaceutical agent is typically released from the matrix according to the release times indicated in (I)(a).

Generally speaking, the outer layer will typically comprise the pharmaceutically active agent in an amount from about 0.001% to about 95% by weight of the outer layer, and the matrix in an amount from about 1% to about 99% by weight of the outer layer. More typically, the outer layer will comprise the pharmaceutically active agent in an amount from about 0.1% to about 30% by weight of the outer layer, and the matrix in an amount from about 60% to about 90% by weight of the outer layer. In each embodiment, the outer layer may comprise a binder in an amount from about 0.1% to about 25% by weight of the outer layer and a filler in an amount from about 0.1% to about 75% by weight of the outer layer. More typically, the outer layer may comprise a binder in an amount from about 0.1% to about 10% by weight of the outer layer and a filler in an amount from about 0.1% to about 25% by weight of the outer layer.

ii. Inner Core

The inner core, if present, is generally coated with the outer layer comprising the matrix and plurality of pharmaceutically active agents or encapsulated pharmaceutically active agents. Without being bound to any particular theory, the inner core is desirable in certain embodiments to provide greater uniformity for drug delivery, and to provide more surface area to which the outer layer may be applied. In this context, the inner core provides a means to increase the amount of pharmaceutically active agent that may be added to the particles while maintaining uniform dosage forms. The inner core comprises an inert material, and may optionally include an indicator coating. In certain embodiments, the inner core is substantially soluble such that is dissolves when contacted with an aqueous medium. In other embodiments, the inner core is substantially insoluble such that it does not dissolve when contacted with an aqueous medium.

The inert material forming the inner core may comprise a variety of suitable materials to the extent they are substantially non reactive with other materials forming the composition of the invention, and in particular, the pharmaceutically active layer. In some embodiments, the suitable materials include without limitation nonpareil sugar beads, tapioca starch beads, complex alumosilcate granules, activated charcoal granules, and sugar compositions. In an exemplary embodiment, the inert material comprises a sugar composition.

Generally speaking, the size of the inner core can and will vary. The inner core may range from about 50 microns to approximately 500 times greater by weight than the weight of the pharmaceutically active agent. In other embodiments, the inner core may be from about 5 times, 10 times, 15 times, 20 times, 25 times, 30 times, 35 times, 40 times, 45 times, 50 times, 55 times, 60 times, 65 times, 70 times, 75 times, 80 times, 90 times, 95 times, 100 times or greater than 250 times greater by weight than the weight of the pharmaceutically active agent. Stated another way, weight ratio of the inner core to the outer layer may be from about 0% to about 10%, from about 5% to about 25%, from about 20% to about 60%, or from about 50% to about 75% by weight of the outer layer. If the inner core is substantially insoluble, it is typically larger than the aperture of the drinking device.

In another embodiment, the inner core may substantially dissolve when contacted with an aqueous medium. In one alternative of this embodiment, the inner core may dissolve after the matrix has substantially eroded. Alternatively, the inner core may dissolve approximately simultaneously as the matrix erodes.

As an aide to determine when the desired amount of pharmaceutically active agent has been administered to the subject, an indicator coating, such as a color indicator or a luminescent indicator, may be formed over the inner core (i.e., disposed between the inner core and outer layer), within the inner core, or may be disposed in the outer layer. The mechanism of detection utilized in the indicator system can and will vary. The mechanism may be based on smell, sight, taste, or touch. In an exemplary embodiment, a color indicator detectable by sight is utilized. By way of non-limiting example, when the indicator coating comprises acryl-Eze red, the coating becomes visible as the pharmaceutically active agent is released from the matrix when the matrix is contacted with an aqueous medium. In another embodiment, the inner core may be colored throughout. Suitable color indicators are generally substantially insoluble when contacted with an aqueous medium and include acryl-Eze, lakes, and other food and FD&C dyes. By way of further non-limiting example, the inner core may be substantially soluble when contacted with an aqueous medium after the matrix erodes. For this embodiment, the inner core may release a flavor into the aqueous medium to indicate when the pharmaceutically active agent has been released. Alternatively, the inner core may release a color, which changes the color of the aqueous medium to indicate when the pharmaceutically active agent has been released.

In another alternative embodiment, the inner core may comprise a luminescent agent as an indicator coating. Suitable luminescent agents include chemiluminescent compounds, such as, e.g., luminol, isoluminol, peroxyoxalates (e.g., bis(2,4,6-trichlorophenyl)oxalate), bioluminescent compounds, such as, e.g., luciferin/luciferase pairs, and fluorescent compounds, e.g., fluorescein and its derivatives. By way of non-limiting example, a luminescent agent may be incorporated into the inner core such that when the outer layer erodes when contacted with a liquid medium, the luminescent agent in the core undergoes a chemical reaction causing it to emit light, which indicates that the pharmaceutically active agent has been administered to the subject. Alternatively, a luminescent agent may be incorporated into the outer layer. In this embodiment, the liquid medium will glow as the outer layer erodes. After the pharmaceutically active agent has been administered to the subject, the glow from the luminescent agent is typically substantially extinguished.

An inner core coated with an indicator coating will generally comprise an inert material in an amount from about 70% to about 90% by weight of the inner core and an indicator coating in an amount from about 10% to about 30% by weight of the inner core. In another embodiment, the inner core coated with an indicator coating will comprise an inert material in an amount from about 75% to about 99% and an indicator coating in an amount from about 1% to about 10% by weight of the inner core. More typically, the inner core coated with an indicator coating will comprise an inert material in an amount from about 80% to about 90% by weight of the inner core and an indicator coating in an amount from about 10% to about 20% by weight of the inner core. The indicator coating may be applied to the inner core by any of the methods detailed herein or as otherwise known in the art.

(c) Excipients

The particle may include one or more suitable excipients. Non-limiting examples of suitable excipients include an agent selected from the group consisting of non-effervescent disintegrants, a coloring agent, a flavor-modifying agent, an oral dispersing agent, a stabilizer, a preservative, a diluent, a compaction agent, a lubricant, a filler, a binder, and an effervescent disintegration agent. The amount and types of excipients utilized to form the particle may be selected according to known principles of pharmaceutical science.

In one embodiment, the excipient is a binder. Suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof. The polypeptide may be any arrangement of amino acids ranging from about 100 to about 300,000 daltons. The amount of binding agent may range from about 0.1% to about 25% by weight of the particle. More typically, the amount of binding agent may range from about 0.1% to about 10% by weight of the particle.

In another embodiment, the excipient may be a filler. Suitable fillers include carbohydrates, inorganic compounds, and polyvynilpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, and sorbitol. The amount of filler may range from about 0.1% to about 75% by weight of the particle. More typically, the amount of filler may range from about 0.1% to about 25% by weight of the particle.

The excipient may comprise a non-effervescent disintegrant. Suitable examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-effervescent disintegrants may be present in an amount from about 2% to about 10% by weight of the particle.

In another embodiment, the excipient may be an effervescent disintegrant. By way of non-limiting example, suitable effervescent disintegrants include sodium bicarbonate in combination with citric acid and sodium bicarbonate in combination with tartaric acid. The effervescent disintegrants may be present in an amount from about 2% and about 10% by weight of the particle.

The excipient may comprise a preservative. Suitable examples of preservatives include antioxidants, such as α-tocopherol or ascorbate, and antimicrobials, such as parabens, chlorobutanol or phenol. The preservative is generally present in an amount of from about 0.001% to about 0.3% by weight of the particle.

In another embodiment, the excipient may include a diluent. Diluents suitable for use include pharmaceutically acceptable saccharide such as sucrose, dextrose, lactose, microcrystalline cellulose, fructose, xylitol, and sorbitol; polyhydric alcohols; a starch; pre-manufactured direct compression diluents; and mixtures of any of the foregoing. The diluents are generally present in an amount of from about 1% to about 10% by weight of the particle.

The excipient may include flavors. Flavors incorporated into the outer layer may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oil, such as lemon oil, orange oil, grape and grapefruit oil, fruit essences including apple, peach, pear, strawberry, raspberry, cherry, plum, pineapple, and apricot. Typically, flavors may be present in an amount ranging from about 0.001% to 3.0% by weight of the particle.

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof. Sweeteners may be present in an amount ranging from about 0.001% to 3.0% by weight of the particle.

In another embodiment, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil. The lubricant may be used in an amount ranging from about 0.001% to about 4% by weight of the particle.

The excipient may be a dispersion enhancer. Suitable dispersants may include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants. The dispersion enhancer may be used in an amount ranging from about 1% to about 10% by weight of the particle.

Depending upon the embodiment, it may be desirable to provide a coloring agent in the particle. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in the present invention depending on the embodiment. Generally speaking, the coloring agent may be present in an amount ranging from about 0.1% to 3.5% by weight of the particle.

(d) Pharmaceutically Active Agent

The particle may be formulated to include any desired pharmaceutically active agent useful in the practice of the present invention. In certain embodiments, the pharmaceutically active agent may be encapsulated by a coating. Irrespective of whether the pharmaceutically active is encapsulated, it may comprise systemically distributable pharmaceutical ingredients such as, vitamins, minerals, and dietary supplements. Alternatively, the pharmaceutically active agent may include non-systemically distributable drugs. The pharmaceutically active agent may also include combinations of two, three, or four or more systemically distributable pharmaceutical ingredients or non-systemically distributable drugs.

(i) Exemplary Pharmaceuticals

Suitable pharmaceutically active agents and enantiomers and derivatives thereof, include, without limitation, an opioid analgesic agent (e.g., as morphine, hydromorphone, oxymorphone, levophanol, methadone, meperidine, fentanyl, codeine, hydrocodone, oxycodone, propoxyphene, buprenorphine, butorphanol, pentazocine and nalbuphine); a non-opioid analgesic agent (e.g., acetylsalicylic acid acetaminophen, paracetamol, ibuprofen, ketoprofen, indomethacin, diflunisol, naproxen, ketorolac, dichlophenac, tolmetin, sulindac, phenacetin, piroxicam, and mefamanic acid); an anti-inflammatory agent (e.g., glucocorticoids such as alclometasone, fluocinonide, methylprednisolone, triamcinolone and dexamethasone; and non-steroidal anti-inflammatory drugs such as celecoxib, deracoxib, ketoprofen, lumiracoxib, meloxicam, parecoxib, rofecoxib, and valdecoxib); an antitussive agent (e.g., dextromethorphan, codeine, hydrocodone, caramiphen, carbetapentane, and dextromethorphan); an antipyretic agent (e.g., acetylsalicylic acid and acetaminophen); an antibiotic agent (e.g., aminoglycosides such as, amikacin, gentamicin, kanamycin, neomycin, netilmicin, streptomycin, and tobramycin; carbecephem such as loracarbef; carbapenems such as certapenem, imipenem, and meropenem; cephalosporins such as cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone; macrolides such as azithromycin, clarithromycin, dirithromycin, erythromycin, and troleandomycin; monobactam: penicillins such as amoxicillin, ampicillin, carbenicillin, cloxacillin, dicloxacillin, nafcillin, oxacillin, penicillin G, penicillin V, piperacillin, and ticarcillin; polypeptides such as bacitracin, colistin, and polymyxin B; quinolones such as ciprofloxacin, enoxacin, gatifloxacin, levofloxacin, lomefloxacin, moxifloxacin, norfloxacin, ofloxacin, and trovafloxacin sulfonamides such as mafenide, sulfacetamide, sulfamethizole, sulfasalazine, sulfisoxazole, and trimethoprim-sulfamethoxazole; and tetracyclines such as demeclocycline, doxycycline, minocycline, and oxytetracycline); an antimicrobial agent (e.g., ketoconazole, amoxicillin, cephalexin, miconazole, econazole, acyclovir, and nelfinavir); a steroidal agent (e.g., estradiol, testosterone, cortisol, aldosterone, prednisone, and cortisone); an amphetamine stimulant agent (e.g., amphetamine); a non-amphetamine stimulant agent (e.g., methylphenidate, nicotine, and caffeine); a laxative agent (e.g., bisacodyl, casanthranol, senna, and castor oil); an anorexic agent (e.g., fenfluramine, dexfenfluramine, mazindol, phentermine, and aminorex); an antihistaminic agent (e.g., phencarol, cetirizine, cinnarizine, ethamidindole, azatadine, brompheniramine, hydroxyzine, and chlorpheniramine); an antiasthmatic agent (e.g., zileuton, montelukast, omalizumab, fluticasone, and zafirlukast); an antidiuretic agent (e.g., desmopressin, vasopressin, and lypressin); an antiflatulent agent (e.g., simethicone); an antimigraine agent (e.g., naratriptan, frovatriptan, eletriptan, dihydroergotamine, zolmitriptan, almotriptan, and sumatriptan); an antispasmodic agent (e.g., dicyclomine, hyoscyamine, and peppermint oil); an antidiabetic agent (e.g., methformin, acarbose, miglitol, pioglitazone, rosiglitazone, troglitazone, nateglinide, repaglinide, mitiglinide, saxagliptin, sitagliptine, vildagliptin, acetohexamide, chlorpropamide, gliclazide, glimepiride, glipizide, glyburide, tolazamide, and tolbutamide); an antacid (e.g., aluminium hydroxide, magnesium hydroxide, calcium carbonate, sodium bicarbonate, and bismuth subsalicylate); a respiratory agent (e.g., albuterol, ephedrine, metaproterenol, and terbutaline); a sympathomimetic agent (e.g., pseudoephedrine, phenylephrine, phenylpropanolamine, epinephrine, norepinephrine, dopamine, and ephedrine); an $H_2$ blocking agent (e.g., cimetidine, famotidine, nizatidine, and ranitidine); an antihyperlipidemic agent (e.g., clofibrate, cholestyramine, colestipol, fluvastatin, atorvastatin, genfibrozil, lovastatin, niacin, pravastatin, fenofibrate, colesevelam, and simvastatin); an antihypercholesterol agent (e.g., lovastatin, simvastatin, pravastatin, fluvastatin, atorvastatin, cholestyramine, colestipol, colesevelam, nicotinic acid, gemfibrozil, and ezetimibe); a cardiotonic agent (e.g., digitalis, ubidecarenone, and dopamine); a vasodilating agent (e.g., nitroglycerin, captopril, dihydralazine, diltiazem, and isosorbide dinitrate); a vasocontricting agent (e.g., dihydroergotoxine and dihydroergotamine); a sedative agent (e.g., amobarbital, pentobarbital, secobarbital, clomethiazole, diphenhydramine hydrochloride, and alprazolam); a hypnotic agent (e.g., zaleplon, zolpidem, eszopiclone, zopiclone, chloral hydrate, and clomethiazole); an anticonvulsant agent (e.g., lamitrogene, oxycarbamezine, pheytoin, mephenyloin, ethosuximide, methsuccimide, carbamazepine, valproic acid, gabapentin, topiramate, felbamate, and phenobarbital); a muscle relaxing agent (e.g., baclofen, carisoprodol, chlorzoxazone, cyclobenzaprine, dantrolene sodium, metaxalone, orphenadrine, pancuronium bromide, and tizanidine); an antipsychotic agent (e.g., phenothiazine, chlorpromazine, fluphenazine, perphenazine, prochlorperazine, thioridazine, trifluoperazine, haloperidol, droperidol, pimozide, clozapine, olanzapine, risperidone, quetiapine, ziprasidone, melperone, and paliperidone); an antianxiolitic agent (e.g., lorazepam, alprazolam, clonazepam, diazepam, buspirone, meprobamate, and flunitrazepam); an antihyperactive agent (e.g., methylphenidate, amphetamine, and dextroamphetamine); an antihypertensive agent (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril); an anti-neoplasia agent (e.g., taxol, actinomycin, bleomycin $A_2$, mitomycin C, daunorubicin, doxorubicin, epirubicin, idarubicin, and mitoxantrone); a soporific agent (e.g., zolpidem tartrate, eszopiclone, ramelteon, and zaleplon); a tranquilizer (e.g., alprazolam, clonazepam, diazepam, flunitrazepam, lorazepam, triazolam, chlorpromazine, fluphenazine, haloperidol, loxapine succinate, perphenazine, prochlorperazine, thiothixene, and trifluoperazine); a decongestant (e.g., ephedrine, phenylephrine, naphazoline, and tetrahydrozoline); a beta blocker (e.g., levobunolol, pindolol, timolol maleate, bisoprolol, carvedilol, and butoxamine); an alpha blocker (e.g., doxazosin, prazosin, phenoxybenzamine, phentolamine, tamsulosin, alfuzosin, and terazosin); a non-steroidal hormone (e.g., corticotropin, vasopressin, oxytocin, insulin, oxendolone, thyroid hormone, and adrenal hormone); a herbal agent (e.g., glycyrrhiza, aloe, garlic, nigella sativa, rauwolfia, St John's wort, and valerian); an enzyme (e.g., lipase, protease, amylase, lactase, lysozyme, and urokinase); a humoral agent (e.g., prostaglandins, natural and synthetic, for example, $PGE_1$, $PGE_2$alpha, and $PGF_2$alpha, and the $PGE_1$ analog misoprostol); a psychic energizer (e.g., 3-(2-aminopropy)indole and 3-(2-aminobutyl)indole); a vitamin (e.g., retinol, retinal, retinoic acid, 3-dehydroretinol, thiamine, riboflavin, niacin, pantothenic acid, pyridoxine, biotin, folic acid, cyanocobalamin, ascorbic acid, lumisterol, ergocalciferol, cholecalciferol, dihydrotachysterol, tocopherol, and naphthoquinone); a mineral (e.g., calcium, iron, zinc, selenium, copper, iodine, magnesium, phosphorus, and chromium); an anti-nausea agent (e.g., dolasetron, granisetron, ondansetron, tropisetron, meclizine, and cyclizine); a hematinic agent (e.g., ferrous salts, ferrous amino chelates, ferrous sulfate, ferrous fumarate, Ferrochel iron, and Sumalate iron); a nutritional product (e.g., bee pollen, bran, wheat germ, kelp, cod liver oil, ginseng, and fish oils, amino acids, proteins, and mixtures thereof); and a fiber product (e.g., cellulose, lignin, waxes, chitins, pectins, beta-glucans, inulin, and oligosaccharides).

(ii) Effective Amounts and Particle Size

The amount of pharmaceutically active agent (or microencapsulated pharmaceutically active agent) embedded in or contained within the particle may be selected according to known principles of pharmacy. Generally speaking, a dosage form that comprises an "effective amount" of pharmaceutically active agent is specifically contemplated. When the term "effective amount" refers to pharmaceuticals, a pharmaceutically effective amount is contemplated. In this context, a pharmaceutically effective amount is the amount or quantity of a drug or pharmaceutically active agent that is sufficient to elicit the required or desired therapeutic response. Alternatively, when the term "effective amount" refers to a vitamin or mineral, it quantifies an amount at least about 10% of the United States Recommended Daily Allowance ("RDA") of that particular ingredient, i.e., vitamin or mineral, for a subject. It is contemplated, however, that amounts of certain minerals or vitamins exceeding the RDA may be beneficial for certain subjects. For example, the amount of a given vitamin or mineral may exceed the applicable RDA by 100%, 200%, 300%, 400% or 500% or more.

As will be appreciated by a skilled artisan, the amount of pharmaceutically active agent embedded in or contained within the particle can vary widely from 0.01 micrograms to 10 grams or more. More typically, the amount will range from a few milligrams to tens of milligrams to several hundred milligrams or more.

The particle size of the ingredients forming the pharmaceutical composition may be an important factor that can effect bioavailability, blend uniformity, segregation, and flow properties. The particle size of the drug and excipients can also affect the suspension properties of the pharmaceutical formulation. For example, smaller particles are less likely to settle and therefore form better suspensions for oral delivery. In various embodiments, the average particle size of the dry powder of the various ingredients is less than about 500 microns in diameter, or less than about 450 microns in diameter, or less than about 400 microns in diameter, or less than about 350 microns in diameter, or less than about 300 microns in diameter, or less than about 250 microns in diameter, or less than about 200 microns in diameter, or less than about 150 microns in diameter, or less than about 100 microns in diameter, or less than about 75 microns in diameter, or less than about 50 microns in diameter, or less than about 25 microns in diameter, or less than about 15 microns in diameter. In some applications the use of particles less than 15 microns in diameter may be advantageous. In these cases colloidal or nano-sized particles in the particle size range of 15 microns down to 10 nanometers may be advantageously employed.

(iii) Controlled Release Formulations

The pharmaceutical agents of the invention may be formulated for the controlled, sustained or timed release of one or more of the ingredients. In this context, typically one or more of the ingredients forming the pharmaceutical composition is microencapsulated or dry coated prior to being embedded in a particle of the invention. By varying the amount and type of coating and its thickness, the timing and location of release of a given ingredient or several ingredients (in either the same dosage form, such as a multi-layered capsule, or different dosage forms) may be varied. Moreover, encapsulation provides a means to mask the taste of the pharmaceutical as it passes through the subject's oral cavity.

The coating can and will vary depending upon a variety of factors, including, the particular ingredient, and the purpose to be achieved by its encapsulation (e.g., flavor masking, maintenance of structural integrity, or formulation for time release). The coating material may be a biopolymer, a semi-synthetic polymer, or a mixture thereof. The microcapsule may comprise one coating layer or many coating layers, of which the layers may be of the same material or different materials. In one embodiment, the coating material may comprise a polysaccharide or a mixture of saccharides and glycoproteins extracted from a plant, fungus, or microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In another embodiment, the coating material may comprise a protein. Suitable proteins include, but are not limited to, gelatin, casein, collagen, whey proteins, soy proteins, rice protein, and corn proteins. In an alternate embodiment, the coating material may comprise a fat or oil, and in particular, a high temperature melting fat or oil. The fat or oil may be hydrogenated or partially hydrogenated, and preferably is derived from a plant. The fat or oil may comprise glycerides, free fatty acids, fatty acid esters, or a mixture thereof. In still another embodiment, the coating material may comprise an edible wax. Edible waxes may be derived from animals, insects, or plants. Non-limiting examples include beeswax, lanolin, bayberry wax, carnauba wax, and rice bran wax. The coating material may also comprise a mixture of biopolymers. As an example, the coating material may comprise a mixture of a polysaccharide and a fat.

In an exemplary embodiment, the coating may be an enteric coating. The enteric coating generally will provide for controlled release of the ingredient, such that drug release can be accomplished at some generally predictable location in the lower intestinal tract below the point at which drug release would occur without the enteric coating. In certain embodiments, multiple enteric coatings may be utilized. Multiple enteric coatings, in certain embodiments, may be selected to release the ingredient or combination of ingredients at various regions in the lower gastrointestinal tract and at various times.

The enteric coating is typically, although not necessarily, a polymeric material that is pH sensitive. A variety of anionic polymers exhibiting a pH-dependent solubility profile may be suitably used as an enteric coating in the practice of the present invention to achieve delivery of the active to the lower gastrointestinal tract. Suitable enteric coating materials include, but are not limited to: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). Combinations of different coating materials may also be used to coat a single capsule.

The thickness of a microcapsule coating may be an important factor in some instances. For example, the "coating weight," or relative amount of coating material per dosage form, generally dictates the time interval between oral ingestion and drug release. As such, a coating utilized for time release of the ingredient or combination of ingredients into the gastrointestinal tract is typically applied to a sufficient thickness such that the entire coating does not dissolve in the gastrointestinal fluids at pH below about 5, but does dissolve at pH about 5 and above. The thickness of the coating is generally optimized to achieve release of the ingredient at approximately the desired time and location.

As will be appreciated by a skilled artisan, the encapsulation or coating method can and will vary depending upon the ingredients used to form the pharmaceutical composition and coating, and the desired physical characteristics of the microcapsules themselves. Additionally, more than one encapsulation method may be employed so as to create a multi-layered microcapsule, or the same encapsulation method may be employed sequentially so as to create a multi-layered microcapsule. Suitable methods of microencapsulation may include spray drying, spinning disk encapsulation (also known as rotational suspension separation encapsulation), supercritical fluid encapsulation, air suspension microencapsulation, fluidized bed encapsulation, spray cooling/chilling (including matrix encapsulation), extrusion encapsulation, centrifugal extrusion, coacervation, alginate beads, liposome encapsulation, inclusion encapsulation, colloidosome encapsulation, sol-gel microencapsulation, and other methods of microencapsulation known in the art. Detailed information concerning materials, equipment and processes for preparing coated dosage forms may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6$^{th}$ Ed. (Media, Pa.: Williams & Wilkins, 1995).

(e) Manufacture of the Particle

The particles of the present invention can be manufactured by conventional pharmacological techniques into a variety of suitable forms, including crystallization, agglomeration, size reduction, and microencapsulation. Conventional pharmacological manufacturing techniques include, e.g., one or a combination of methods: (1) dry mixing, (2) direct compression, (3) milling, (4) dry or non-aqueous granulation, (5) wet granulation, or (6) fusion. Other methods include, e.g., prilling, spray drying, pan coating, melt granulation, granulation, wurster coating, tangential coating, top spraying, extruding, coacervation and the like. Detailed information concerning materials, equipment and processes for preparing a particle by any of these techniques may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6$^{th}$ Ed. (Media, Pa.: Williams & Wilkins, 1995).

(II) Drinking Device

The drinking device is not a critical feature of the invention to the extent that its volume and design are considered during the spatial arrangement of the plurality of particles, as more fully described in the Examples. Typically the drinking device may comprise a hollow tube having two ends that may be filled with a plurality of particles to form a fill bed. In an exemplary embodiment, the drinking device is a straw. By way of example, FIG. 4 presents suitable alternate designs for the drinking device, which include, a hollow tube with ribs or baffles (FIG. 4A), an octagonal hollow tube (FIG. 4B), and a flat hollow tube (FIG. 4C).

The size of the drinking device can and will vary depending upon the embodiment. By way of example, the drinking device may comprise a hollow circular tube from about 1 to about 20 mm in diameter, and from about 50 to about 500 mm in length. The drinking device may be from about 2 to about 4 mm in diameter, from about 4 to about 6 mm in diameter, from about 6 to about 8 mm in diameter, from about 8 to about 10 mm in diameter, from about 10 to about 12 mm in diameter, from about 12 to about 14 mm in diameter, from about 14 to about 16 mm in diameter, from about 16 to about 18 mm in diameter, from about 18 to about 20 mm in diameter, or greater than about 20 mm in diameter. The drinking device may be from about 25 to about 50 mm in length, from about 50 to about 75 mm in length, from about 75 to about 100 mm in length, from about 100 to about 125 mm in length, from about 125 to about 150 mm in length, from about 150 to about 175 mm in length, from about 175 to about 200 mm in length, from about 200 to about 225 mm in length, from about 225 to about 250 mm in length, from about 250 to about 275 mm in length, from about 275 to about 300 mm in length, from about 300 to about 325 mm in length, from about 325 to about 350 mm in length, from about 350 to about 375 mm in length, from about 375 to about 400 mm in length, from about 400 to about 425 mm in length, from about 425 to about 450 mm in length, from about 450 to about 475 mm in length, from about 475 to about 500 mm in length, or greater than about 500 mm in length.

The drinking device is generally equipped with particle containment elements that restrain the plurality of particles within the hollow tube, but allow fluid to pass through the device as the subject imbibes the fluid. The containment elements could be in the form of perforated end-caps, porous plugs, or may be the particles of the invention, such as particles that have been interlocked. In an exemplary embodiment, the containment elements are placed within the device so that fluid flow is laminar and in substantially one direction path (i.e., from the container containing the fluid, through the drinking device, and into the mouth of the subject).

(III) Spatial Arrangement of Particles in a Drinking Device

A plurality of the particles described in (I) above are spatially arranged within a drinking device described in (II) under conditions such that a dosage of an effective amount of a pharmaceutical is orally administered to the subject as fluid flows around and/or through the particles via the drinking device. Several parameters impact accurate delivery of the pharmaceutical to the subject. These parameters include, but are not limited to, the physical and/or chemical properties of the particles, the volume and design of the device, and the properties of the fluid and parameters of its flow through the device. Varying one or more of these parameters can optimize the amount and rate of pharmaceutical delivery.

The number of particles comprising the "plurality" can and will vary significantly depending upon their size and the volume of the delivery device's fill bed. The number of particles may range from 2 to greater than about 10,000. Stated another way, from about 1% to about 99% of the volume of the fill bed may be occupied by particles. In other embodiments, from about 1% to about 10%, from about 10% to about 20%, from about 20% to about 30%, from about 30% to about 40%, from about 50% to about 60%, from about 60% to about 70%, from about 70% to about 80%, from about 80% to about 90%, or from about 90% to 100% of the volume of the fill bed may be occupied by particles. The particles may all comprise pharmaceutically active agents. Alternatively, some of the particles may comprise pharmaceutically active agents and some of the particles may not comprise pharmaceutically active agents.

(a) Specific Flow Resistance

The plurality of particles may be spatially arranged within a drinking device to achieve a specific flow resistance such that a dosage comprising an effective amount of the pharmaceutically active agent is orally delivered to the subject as fluid flows over the particles. The flow resistance of a plurality of particles (i.e., pressure drop across the bed) depends on several factors, including the shape of the particles and their packing arrangement, as well as the depth of the bed, and the linear velocity, density, and viscosity of the fluid. The Examples delineate methods and formulas that may be utilized by a skilled artisan to vary one or more of the foregoing parameters in order to achieve a desired specific flow resistance. Typically, the specific flow resistance is not greater than about 50 Torr/mm. The specific flow resistance may range from about 0 to about 50 Torr/mm. In other embodiments, the specific flow resistance may be about 1 Torr/mm, about 2 Torr/mm, about 3 Torr/mm, about 4 Torr/mm, about 5 Torr/mm, about 6 Torr/mm, about 7 Torr/mm, about 8 Torr/mm, about 9 Torr/mm, about 10 Torr/mm, about 11 Torr/mm, about 12 Torr/mm, about 13 Torr/mm, about 14 Torr/mm, about 15 Torr/mm, about 16 Torr/mm, about 17 Torr/mm, about 18 Torr/mm, about 19 Torr/mm, about 20 Torr/mm, about 21 Torr/mm, about 22 Torr/mm, about 23 Torr/mm, about 24 Torr/mm, or greater than about 25 Torr/mm.

(b) Interstitial Porosity

The plurality of particles may be spatially arranged within a drinking device to achieve an interstitial porosity of the bed of particles such that a dosage comprising an effective amount of the pharmaceutically active agent is orally delivered to the subject as fluid flows over the particles. Interstitial porosity of the bed is generally determined by the packing of particles and is dependent upon their size and shape in relation to the size and shape of the drinking device. It may be determined as the ratio of the volume of the void space (i.e., volume of the bed not occupied by beads) to the volume of the bead. Generally particles having a size and shape that allow for relatively close packing tend to have less interstitial porosity compared to particles having a size and shape that allow for relatively loose packing. As illustrated in the examples, all other parameters being equal, spherical particles with "close" hexagonal packing generally have a computed interstitial porosity of 0.2595 (i.e., about 26%), whereas spherical particles with "loose" cubic packing generally have a computed interstitial porosity of 0.4764 (i.e., about 48%). The plurality of particles are generally selected and spatially arranged so that the interstitial porosity is not less than about 1%. The interstitial porosity may range from about 1% to about 99%. In some embodiments, the interstitial porosity may be less than about 1%, from about 1% to about 5%, from about 5% to about 10%, from about 10% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 95%, or greater than about 95%.

The interstitial porosity of the plurality of particles may change as fluid flows over the particles without departing from the scope of the invention. Typically, the interstitial porosity may change in embodiments having particles that substantially dissolve or swell when contacted with the fluid. For example the initial interstitial porosity of the plurality of particles (i.e., before fluid has been drawn through the drinking device) may be about 45% and the final interstitial porosity of the particles (i.e., after the dosage comprising an effective amount of pharmaceutical has been administered) may be about 30%. The degree in the change of initial interstitial porosity compared to final interstitial porosity can and will vary from about 0% to about 100%. The degree of change in interstitial porosity may range from 0%, from about 1% to about 10%, from about 10% to about 20%, from about 20% to about 30%, from about 30% to about 40%, from about 40% to about 50%, from about 50% to about 60%, from about 60% to about 70%, from about 70% to about 80%, from about 80% to about 90%, or from about 90% to about 100%.

(c) Rate of Pharmaceutical Administration

The particles may also be selected and spatially arranged in the drinking device to achieve dosage administration in a desired duration of time. In an exemplary embodiment, the particles comprising the pharmaceutically active agent may be predominantly placed at the end opposite the inflow from the liquid receptacle. In this manner, the dosage may be orally administered to the subject in the first few sips of fluid. For example, the particles comprising the pharmaceutically active agent may be placed in the delivery device such the particles are predominantly within the first 5%, about the first 10%, about the first 20%, about the first 30%, about the first 40%, or within about the first 50% of the end opposite the inflow from the liquid receptacle.

In an exemplary embodiment, the plurality of particles are selected and spatially arranged within the drinking device so that the dosage of pharmaceutical is orally administered to the subject in from about 1 to about 100 sips. In another embodiment, the dosage of pharmaceutical agent may be administered to the subject in from about 1 to about 5 sips, from about 5 to about 10 sips, from about 10 to about 15 sips, from about 15 to about 20 sips, from about 20 to about 25 sips, from about 25 to about 30 sips, from about 30 to about 35 sips, from about 35 to about 40 sips, from about 40 to about 50 sips, from about 50 to about 55 sips, from about 55 to about 60 sips, from about 60 to about 65 sips, from about 65 to about 70 sips, from about 70 to about 75 sips, from about 75 to about 80 sips, from about 80 to about 85 sips, from about 85 to about 90 sips, from about 90 to about 95 sips, or greater than about 95 sips. Stated another way, the dosage of pharmaceutical agent is typically administered after the subject has imbibed from about 1 to about 100 mL of fluid. In another embodiment, the dosage of pharmaceutical agent is typically administered after the subject has imbibed from about 1 to about 5 mL of fluid, from about 5 to about 10 mL of fluid, from about 10 to about 15 mL of fluid, from about 15 to about 20 mL of fluid, from about 20 to about 25 mL of fluid, from about 25 to about 30 mL of fluid, from about 30 to about 35 mL of fluid, from about 35 to about 40 mL of fluid, from about 40 to about 45 mL of fluid, from about 45 to about 50 mL of fluid, from about 50 to about 55 mL of fluid, from about 55 to about 60 mL of fluid, from about 60 to about 65 mL of fluid, from about 65 to about 70 mL of fluid, from about 70 to about 75 mL of fluid, from about 75 to about 80 mL of fluid, from about 80 to about 85 mL of fluid, from about 85 to about 90 mL of fluid, from about 90 to about 95 mL of fluid, from about 95 to about 100 mL of fluid, or greater than about 100 mL of fluid.

Another factor that may impact release of the pharmaceutical from the particles is the intraparticulate porosity of the particles themselves. The intraparticulate porosity is the ratio of the void volume (not occupied by the solid substance of the particle) to the overall volume of the particle. Typically, the greater intraparticulate porosity of the particles may result in a faster release of the pharmaceutical from the particles. Particles that are substantially porous generally have a higher intraparticulate porosity compared to particles that are substantially non-porous. For example, a particle comprised of a material similar in porosity to a sponge may have an intraparticulate porosity of as high as 99%, whereas a particle comprised of a material similar in porosity to a non-porous crystal may have an intraparticulate porosity of approximately 0%. The plurality of particles are generally selected so that the intraparticulate porosity is not less than about 1%. The intraparticulate porosity may range from about 1% to about 99%. In some embodiments, the intraparticulate porosity may be less than about 1%, from about 1% to about 5%, from about 5% to about 10%, from about 10% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 95%, or greater than about 95%.

(IV) Fluid

The type of fluid utilized to administer the pharmaceutical agent can and will vary without departing from the scope of the invention. For example, the viscosity of the fluid may range from a viscosity similar to water (i.e., 1.002 cP at 20° C.) to a viscosity similar to glycerin (i.e., greater than about 1400 cP at 20° C.). In certain embodiments, viscosity modifiers may be mixed with the fluid. Suitable viscosity modifiers include starches such as cornstarch, potato starch, pregelatinized and modified starches thereof, sweeteners, cellulose, alginates, sodium starch glycolate, gums such as agar, guar, locust bean, karaya, pecitin, and tragacanth.

The fluid may be of a variety of temperatures and pH ranges from acidic, to neutral, to basic. In an exemplary embodiment, the pH and temperature of the fluid may be selected so as to optimize the solubility of the particles and/or pharmaceutical agents. For example, if a particle or pharmaceutical agent is substantially insoluble at a basic pH, then the fluid selected may be a fluid having an acidic to neutral pH. Alternatively, if a particle or pharmaceutical agent is substantially insoluble at an acidic pH, then the fluid selected may be a fluid having a neutral to basic pH.

Non-limiting examples of a fluids suitable for use include milk, flavored milk drinks, goat milk, liquid yogurt, soy milk, rice milk, fruit drinks, fruit-flavored drinks, vegetable drinks, nutritional drinks, energy drinks, sports drinks, infant formula, teas, and coffee drinks.

DEFINITIONS

The term "subject" as used herein includes a wide range of subjects including animals and humans. In an exemplary embodiment, the subject is a human. In a particularly preferred embodiment, the subject is a human that has difficulty swallowing. In one alternative of this embodiment, the subject is a child. In another alternative of this embodiment, the subject is elderly. In a further embodiment, the subject has an illness, such as cancer, Acquired Immune Deficiency Syndrome (AIDS), the flu, pneumonia and other similar illnesses resulting in weakness or a difficulty in swallowing or consuming adequate nutrition. In another alternative embodiment, the subject has undergone a gastric bypass procedure. In still another alternative embodiment, the subject has a medical condition of the oral and pharangeal mucosa. In yet another alternative embodiment, the subject may have mucositis, an oral infection (e.g., candidiasis), or an autoimmune disease (e.g., Bechet's disease, erosive lichen planus, and various pemphigoid manifestations).

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention. For each of examples 1-6 below the drinking device utilized or contemplated is a straw.

Example 1

Hydraulic Analysis of a Drinking Device

A parameter that impacts oral pharmaceutical delivery to a subject by a straw comprising a plurality of particles is its resistance to the flow of liquid. The flow resistance of a plurality of particles (pressure drop across the bed) depends on the shape of the particles and their packing arrangement, as well as the depth of the bed, the linear velocity, density, and viscosity of the liquid.

A liquid flow analysis of a drinking device comprising a hollow tube packed with particles of difference shapes or sizes was conducted using the approach developed in the fields of chemical engineering and soil mechanics. In this example, the device comprised a hollow circular tube of 8 mm in diameter and 180 mm in length that was filled with one of two different types of bed packing: 1) spherical particles with "close" hexagonal packing, with a computed porosity of 0.2595, and 2) spherical particles with "loose" cubic packing, with a computed porosity of 0.4764. The initial depth of the bed was approximately 105 mm. The containment elements of the bed were perforated cone-shaped end caps. The analysis was based on the following assumptions: 1) The bed comprised monodisperse, non-porous spherical particles. 2) The wall effect on the packing of the particles was negligible. (This assumption is reasonable for small particles (about 1/10 of the tube diameter in size). For larger particles, the wall effect would result in the reduced packing density. Therefore, the actual straw resistance to the flow of liquid will be somewhat lower than the computed value.) 3) All of the particles dissolved at the same rate, which was controlled by the actual dissolution of the particle material and was proportional to the surface area of the particle. 4) The dissolution medium was room temperature water. 5) A flow rate of the liquid through the tube was estimated to be approximately 250 ml/min, based on the "sipping process" of a healthy male person.

Figure 1:
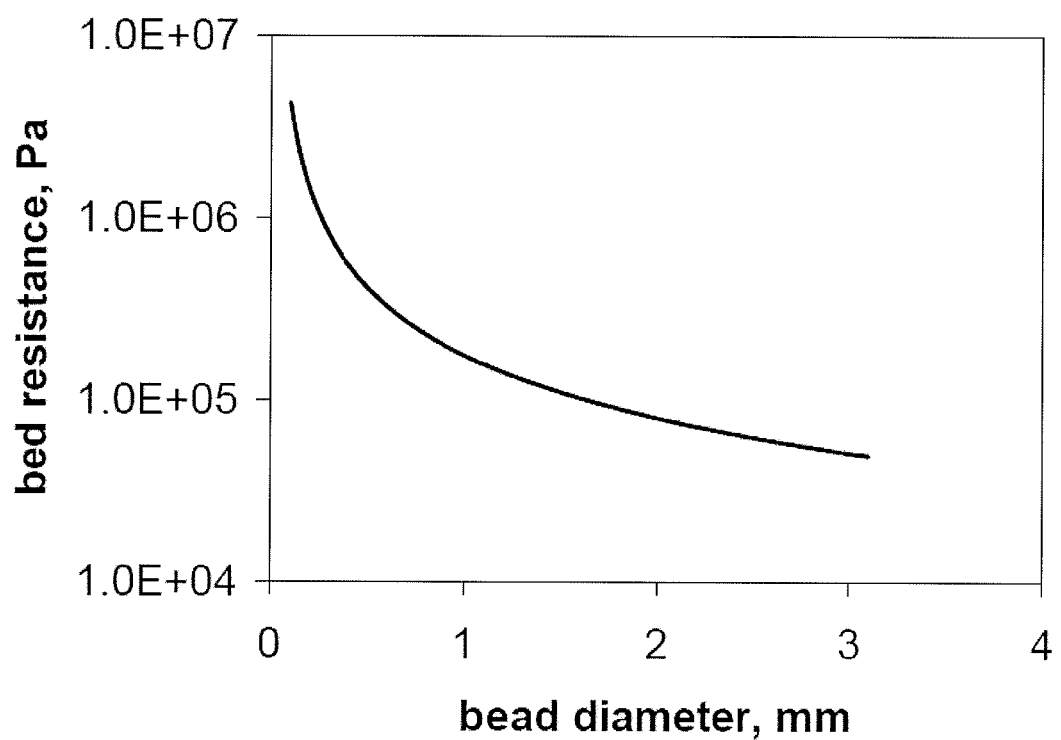
FIG. 1 is a graph depicting the flow resistance of a drinking device having a plurality of particles that are "close" hexagonally packed. Plotted is the change in bed resistance as a function of particle diameter.
Figure 2:
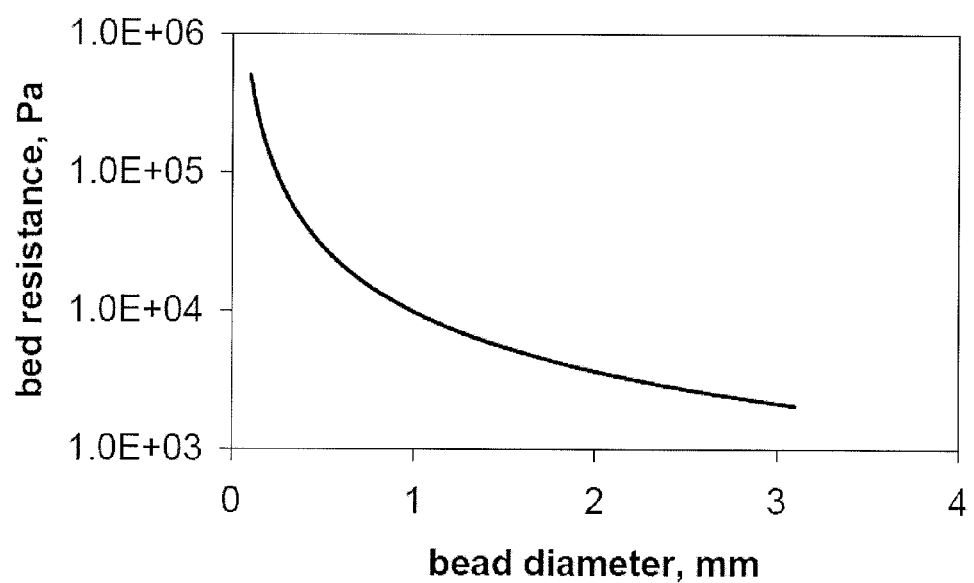
FIG. 2 is a graph depicting the flow resistance of a drinking device having a plurality of particles that are "loose" cubic packed. Plotted is the change in bed resistance as a function of particle diameter.

The initial bed resistance to the flow of liquid for the two types of packing is depicted in FIGS. 1 and 2. This analysis revealed that bed resistance decreased rapidly when the particle diameter was smaller than approximately 1 mm (note the logarithmic scale of the vertical axis on the graphs).

The mass (volume) rate of the material dissolution can be described by the following equation:

$$\frac{d}{dt}V(t) = -kS(t) \tag{1}$$

where V(t) is the particle volume as a function of time, S(t) is the particle surface area as a function of time and k is the dissolution rate constant.

For a spherical particle with the diameter d(t), V(t) and S(t) are:

$$V(t) = \frac{\pi}{6}d(t)^3 \tag{2}$$
$$S(t) = \pi d(t)^2$$

Substitution (2) into (1) and differentiation results in the following linear ordinary differential equation:

$$\frac{d}{dt}d(t) = -2k \tag{3}$$

Solution to the equation (3) is given by the formula:

$$d(t) = d_0 - 2kt \tag{4}$$

where $d_0$ is the initial diameter of the particle at the time t=0.

As the particles dissolve, the bed volume decreases. Assuming the unchanging packing type and, therefore, constant bed porosity, the bed depth, L, will change according to the equation:

$$L(t) = L_0 \left(1 - 2\frac{k}{d_0}t\right)^3 \quad (5)$$

Based on the above, the flow resistance of the hollow tube as a function of time can easily be calculated with the use of the following Mathcad routine:

$$\Delta P(t, d_0) := \begin{vmatrix} d \leftarrow d_0 - 2 \cdot k \cdot t & (6) \\ L \leftarrow L_0 \dfrac{d^3}{d_0^3} \\ Re \leftarrow \begin{vmatrix} \dfrac{0.45 \cdot V_{up} \cdot d \cdot \rho}{\mu \cdot (1-n) \cdot \sqrt{n}} & \text{if } d > 0 \\ 1 & \text{if } d \leq 0 \end{vmatrix} \\ S \leftarrow \begin{vmatrix} \dfrac{1.53 \cdot L}{n^{4.2} \cdot (d)} \cdot \left(\dfrac{30}{Re} + \dfrac{3}{Re^{0.7}} + 0.3\right) \cdot \dfrac{\rho \cdot V_{up}^2}{2} & \text{if } d > 0 \\ 0 & \text{if } d \leq 0 \end{vmatrix} \\ \text{return } S \end{vmatrix}$$

The changes in the flow resistance (pressure drop) of a hollow tube filled with the various initial diameter particles as a function of the "sip" time are plotted in FIG. 3. Any changes in the dissolution kinetics or the initial packing of the particles will result in the either faster or slower decrease of the flow resistance of the device depending on the dissolution rate of the particles. There will be no change in the liquid flow pattern or the character of the bed flow resistance.

This analysis revealed that: 1) the flow resistance of the drinking device strongly depends on the particle diameter and type of packing. 2) The flow resistance of the device steadily declines over the course of the delivery ("sipping") process. 3) The liquid flow through the cylindrical device is laminar with minimal to no convective mixing.

Example 2

Using Particle Size to Control Flow Rate (Flow Resistance) in a Drinking Device

The flow resistance of a drinking device with a hexagonally ("close") packed bed, as described in Example 1, was calculated. If the fluid flow was 250 ml/min, then the initial flow resistance of the device for particles of different diameters is shown in Table 1. If the "sucking effort" normally exerted by a healthy male were approximately 190 Torr, then the flow rate of a tube filled with 1.0 mm particles would be reduced to approximately 85 ml/min.

TABLE 1

Flow resistance as a function of particle diameter.

| Initial Flow Resistance (Torr) | Particle diameter (mm) |
|---|---|
| 192 | 2.8 |
| 301 | 2.0 |
| 449 | 1.5 |
| 814 | 1.0 |

Example 3

Using Design Elements to Control Flow Rate in a Drinking Device

The shape or overall design of a drinking device will also tested to determine how it affects flow rate (flow resistance). For example, the drinking device may be a ribbed hollow tube (FIG. 4A). It is predicted that a tube with ribs or baffles would have packing that is intermediate in density between the "close" hexagonal type and the "loose" cubic type. Alternatively, the hollow tube may have an octagonal (or another non-circular) shape (FIG. 4B). Such a design may facilitate cubic "loose" packing, resulting in decreased flow resistance. In another alternative, the device may be a flat hollow tube (FIG. 4C). If such a device were filled with large diameter particles, then the device would have a very low flow resistance.

Example 4

Using Insoluble Carrier Particles to Control the Flow Rate in a Drinking Device

Another strategy to control flow and affect release of the active ingredient would be to fill a drinking device with insoluble carrier particles, whereby the flow would be regulated and the active ingredient would be released via a desorption mechanism. The bed of inert insoluble carrier particles would impart a predetermined flow resistance that would limit the liquid flow rate through the device, and hence, set a predetermined treatment duration of a given liquid volume.

Example 5

Particles Comprising an Active Ingredient Whose Release is via Zero Order Kinetics A drinking device will be tested that is filled with particles in which the active pharmaceutical ingredient is released by zero order kinetics, e.g., diffusion or erosion controlled mechanisms. Particles with these characteristics would be well suited to deliver active pharmaceutical ingredients to the specific sites, such as in the mouth or the throat where a prolonged exposure to the drug is required. Examples include the use of Zn in cold treatments, the local delivery of antibiotics or antivirals to mouth sores, the local delivery of anesthesia, and the like. In this example, it is the time of action that controls the dose of the active pharmaceutical ingredient rather than the volume of the consumed liquid.

Example 6

Particles Comprising an Ionizable Active Ingredient Bound to an Ion Exchange Resin A drinking device will be tested that contains an ionizable active pharmaceutical ingredient bound to ion exchange resin particles. A counter ion generator (e.g., a salt or a solid acid or base) will be incorporated into other particles that are either mixed with the ion exchange/active ingredient complex particles or positioned upstream in the flow device. The counter ion release/dissolution kinetics would then govern the release of the active ingredient from the drinking device, provided that the ion exchange reaction is not a rate-limiting step of the process. The counter ion generator would be selected in such a way, that it provides all necessary ions for the desired drug form. One example for such a device would be the release of diphenhydramine (DPH) HCl from a diphenhydramine/ion exchange resin complex, with calcium chloride being used as the ion generator. Calcium cations would release DPH from the complex and chloride anions will bind with DPH to form DPH HCl.

What is claimed is:

1. A method of delivering a pharmaceutically active agent to a subject, the method comprising:
a subject imbibing an aqueous fluid using a drinking device, wherein the drinking device comprises a hollow tube having two ends, a plurality of particles, each of the plurality of particles comprising a pharmaceutically active agent, and the device further comprising a plurality of particle containment elements that restrain the particles within the hollow tube while the subject imbibes the aqueous fluid and a dosage comprising an effective amount of the pharmaceutically active agent is orally delivered to the subject as fluid flows over the plurality of particles during said imbibing, wherein the particles are spatially arranged within the device to achieve a specific flow resistance not greater than about 50 Torr/mm such that a dosage comprising an effective amount of the pharmaceutically active agent is orally delivered to the subject as fluid flows over the particles during said imbibing, wherein each of the plurality of particles comprises an inner core comprising an inert material, and an outer layer containing the active agent and surrounding the inner core, the inner cores remaining within the hollow tube after said imbibing, and wherein the inner cores are insoluble when contacted with an aqueous medium.

2. The method of claim 1 wherein the drinking device is in the form of a straw.

3. The method of claim 2 wherein the particles comprising a pharmaceutically active agent are spatially arranged at the end of the straw where the subject imbibes the aqueous fluid.

4. The method of claim 1 wherein the dosage of the pharmaceutically active agent is orally administered after the subject has imbibed from about 10 to about 50 mL of the aqueous fluid.

5. The method of claim 1, wherein the dosage of the pharmaceutically active agent is orally administered after the subject has imbibed at least about 10 mL of the aqueous fluid.

6. The method of claim 1 wherein the particles release the pharmaceutically active agent within from about 1 second to about 5 minutes after being contacted with the aqueous fluid.

7. A method of delivering a pharmaceutically active agent to a subject, the method comprising:
a subject imbibing an aqueous fluid using a drinking device, wherein the drinking device comprises a hollow tube having two ends, a plurality of particles, each of the plurality of particles comprising a pharmaceutically active agent and an indicator coating, and the device further comprising a plurality of particle containment elements that restrain the particles within the hollow tube while the subject imbibes the aqueous fluid and a dosage comprising an effective amount of the pharmaceutically active agent is orally delivered to the subject as fluid flows over the plurality of particles during said imbibing, wherein each of the plurality of particles comprises an inner core comprising an inert material, an outer layer surrounding the inner core and containing the active agent, the indicator coating surrounding the inner core and in contact with the outer layer, the inner cores remaining within the hollow tube after said imbibing and wherein the inner cores are insoluble when contacted with an aqueous medium.

8. The method of claim 7 wherein the drinking device is in the form of a straw.

9. The method of claim 8 wherein the particles comprising a pharmaceutically active agent are spatially arranged at the end of the straw where the subject imbibes the aqueous fluid.

10. The method of claim 7 wherein the dosage of the pharmaceutically active agent is orally administered after the subject has imbibed from about 10 to about 50 mL of the aqueous fluid.

11. The method of claim 7, wherein the dosage of the pharmaceutically active agent is orally administered after the subject has imbibed at least about 10 mL of the aqueous fluid.

12. The method of claim 7 wherein the particles release the pharmaceutically active agent within from about 1 second to about 5 minutes after being contacted with the aqueous fluid.

13. The method of claim 7 wherein the indicator coating comprises a color such that when the dosage of the pharmaceutically active agent is released from the particles a color becomes visible.

14. The method of claim 7 wherein the particles have a tensile strength of not less than about 0.01 MPa and a friability of not more than about 15%.

15. The method of claim 14 wherein the drinking device is in the form of a straw.

16. The method of claim 15 wherein the particles comprising a pharmaceutically active agent are spatially arranged at the end of the straw where the subject imbibes the aqueous fluid.

17. The method of claim 14 wherein the dosage of the pharmaceutically active agent is orally administered after the subject has imbibed from about 10 to about 50 mL of the aqueous fluid.

18. The method of claim 14, wherein the dosage of the pharmaceutically active agent is orally administered after the subject has imbibed at least about 10 mL of the aqueous fluid.

19. The method of claim 14 wherein the particles release the pharmaceutically active agent within from about 1 second to about 5 minutes after being contacted with the aqueous fluid.

20. The method of claim 14 wherein the particles have a tensile strength ranging from about 0.1 to about 10 MPa, and a friability ranging from about 0% to about 5%.

* * * * *